US008846559B2

(12) United States Patent
Ghosh et al.

(10) Patent No.: US 8,846,559 B2
(45) Date of Patent: Sep. 30, 2014

(54) STABLE SHAPE-SELECTIVE CATALYST FOR AROMATIC ALKYLATION AND METHODS OF USING AND PREPARING

(75) Inventors: Ashim Kumar Ghosh, Houston, TX (US); Neeta Kulkarni, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 459 days.

(21) Appl. No.: 12/263,689

(22) Filed: Nov. 3, 2008

(65) Prior Publication Data

US 2010/0113850 A1    May 6, 2010

(51) Int. Cl.
| | |
|---|---|
| B01J 29/06 | (2006.01) |
| C07C 2/66 | (2006.01) |
| B01J 29/44 | (2006.01) |
| B01J 29/46 | (2006.01) |
| B01J 29/40 | (2006.01) |
| B01J 37/28 | (2006.01) |

(52) U.S. Cl.
CPC .............. B01J 29/44 (2013.01); B01J 2229/18 (2013.01); C07C 2/66 (2013.01); B01J 2229/42 (2013.01); B01J 2229/20 (2013.01); B01J 29/46 (2013.01); B01J 29/40 (2013.01); B01J 2229/37 (2013.01); C07C 2529/44 (2013.01); B01J 37/28 (2013.01)
USPC ................... 502/74; 502/60; 502/63; 502/64; 502/66; 502/71; 502/77

(58) Field of Classification Search
USPC ........................ 502/60, 63, 64, 66, 71, 77, 74
See application file for complete search history.

(56) References Cited

U.S. PATENT DOCUMENTS

| | | | |
|---|---|---|---|
| 3,562,345 A | 2/1971 | Mitsche | |
| 3,702,886 A | 11/1972 | Argauer et al. | |
| 3,950,242 A | 4/1976 | Garwood et al. | |
| 3,962,364 A | 6/1976 | Young | |
| 3,965,207 A | 6/1976 | Weinstein | |
| 4,002,697 A | 1/1977 | Chen | |
| 4,025,606 A | 5/1977 | Acres | |
| 4,100,215 A | 7/1978 | Chen | |
| 4,115,424 A | 9/1978 | Unland et al. | |
| 4,140,726 A | 2/1979 | Unland et al. | |
| 4,152,364 A * | 5/1979 | Chu ............................. | 585/454 |
| 4,250,345 A | 2/1981 | Chu | |
| 4,278,827 A | 7/1981 | Chu et al. | |
| 4,363,750 A | 12/1982 | Rozovsky et al. | |
| 4,377,718 A | 3/1983 | Sato et al. | |
| 4,380,685 A | 4/1983 | Chu | |
| 4,409,132 A | 10/1983 | Forbus et al. | |
| 4,415,477 A | 11/1983 | Rozovsky et al. | |
| 4,417,076 A | 11/1983 | Rozovsky et al. | |
| 4,420,418 A * | 12/1983 | Chu ............................. | 502/77 |
| 4,444,989 A | 4/1984 | Herkes | |
| 4,478,949 A * | 10/1984 | Kaeding ........................ | 502/77 |
| RE31,919 E | 6/1985 | Butter et al. | |
| 4,536,375 A | 8/1985 | Holt et al. | |
| 4,548,914 A * | 10/1985 | Chu ............................... | 502/85 |
| 4,554,394 A * | 11/1985 | Forbus et al. ................. | 585/474 |
| 4,590,321 A | 5/1986 | Chu | |
| 4,623,530 A | 11/1986 | Cullo et al. | |
| 4,623,633 A | 11/1986 | Young | |
| 4,638,106 A | 1/1987 | Pieters et al. | |
| 4,657,884 A | 4/1987 | Luft et al. | |
| 4,665,251 A | 5/1987 | Chu | |
| 4,670,616 A | 6/1987 | De Simone et al. | |
| 4,673,767 A | 6/1987 | Nimry et al. | |
| 4,681,745 A | 7/1987 | Pinto | |
| 4,694,114 A | 9/1987 | Chu et al. | |
| 4,695,442 A | 9/1987 | Pinto et al. | |
| 4,695,666 A | 9/1987 | Chao et al. | |
| 4,695,667 A | 9/1987 | Sumitani et al. | |
| 4,704,495 A | 11/1987 | Dessau | |
| 4,716,135 A | 12/1987 | Chen | |
| 4,721,827 A | 1/1988 | Cullo et al. | |
| 4,727,209 A | 2/1988 | Chao | |
| 4,746,763 A | 5/1988 | Kocal | |
| 4,758,328 A | 7/1988 | Young | |
| 4,761,513 A | 8/1988 | Steacy | |
| 4,781,815 A | 11/1988 | Pellet et al. | |

(Continued)

FOREIGN PATENT DOCUMENTS

JP    61221137 A2    10/1971

OTHER PUBLICATIONS

F.M. Bautista, et al., Toluene Methylation on AlPO4—Al2O3 Catalysts, React. Kinet. Catal. Lett., 1996, pp. 61-70, vol. 57, No. 1.
Oyvind Mikkelsen, et al., Use of Isotopic Labeling for Mechanistic Studies of the Methanol-to-Hydrocarbons reaction. Methylation of toluene with Methanol Over H-ZSM-5, H-Mordenite and H-Beta, Microporous and Mesoporous Materials, 2000, pp. 93-113, vol. 40.
P.G. Smirniotis, et al., Alkylation of Benzene or Toluene with MeOH or C2H4 over ZSM-5 or B-Zeolite: Effect of the Zeolite Pore Openings and of the Hydrocarbons Involved on the Mechanism of Alkylation, Ind. Eng. Chem. Res., 1995, pp. 1517-1528, vol. 34.

(Continued)

Primary Examiner — Elizabeth Wood
(74) Attorney, Agent, or Firm — Cantor Colburn LLP (57) ABSTRACT

A catalyst and method of forming a catalyst for use in aromatic alkylation involves treating a zeolite, which may be a ZSM-5 zeolite, with a phosphorus-containing compound. The phosphorus-treated zeolite is combined with a binder material. The bound phosphorus-treated zeolite is treated with an aqueous solution of a hydrogenating metal compound by contacting the bound phosphorus-treated zeolite with the aqueous solution and separating the aqueous solution from the bound phosphorus-treated zeolite to form a hydrogenating-metal-containing zeolite catalyst. The catalyst may be used in preparing an alkyl aromatic product by contacting a hydrogenating-metal-containing zeolite catalyst with an aromatic alkylation feed of an aromatic compound and an alkylating agent under reaction conditions suitable for aromatic alkylation.

22 Claims, 6 Drawing Sheets

(56) References Cited

U.S. PATENT DOCUMENTS

| | | | |
|---|---|---|---|
| 4,822,943 A * | 4/1989 | Burress | 585/467 |
| 4,847,223 A | 7/1989 | Le Van Mao et al. | |
| 4,861,930 A | 8/1989 | Cottrell et al. | |
| 4,873,067 A | 10/1989 | Valyocsik et al. | |
| 4,891,197 A | 1/1990 | Derouane et al. | |
| 4,891,467 A | 1/1990 | Sikkenga | |
| 4,902,406 A | 2/1990 | Valyocsik | |
| 4,910,007 A | 3/1990 | Pinto et al. | |
| 4,912,073 A | 3/1990 | Chu | |
| 4,914,067 A | 4/1990 | Pellet et al. | |
| 4,935,574 A | 6/1990 | D'Amore et al. | |
| 4,962,255 A | 10/1990 | Fraenkel et al. | |
| 4,973,399 A | 11/1990 | Green et al. | |
| 4,973,781 A | 11/1990 | Valyocsik et al. | |
| 4,980,052 A | 12/1990 | Green et al. | |
| 5,041,402 A | 8/1991 | Casci et al. | |
| 5,043,502 A | 8/1991 | Martindale et al. | |
| 5,047,141 A | 9/1991 | Chu | |
| 5,068,483 A | 11/1991 | Barthomeuf et al. | |
| 5,094,995 A | 3/1992 | Butt et al. | |
| 5,105,047 A | 4/1992 | Waller | |
| 5,108,579 A | 4/1992 | Casci | |
| 5,110,776 A | 5/1992 | Chitnis et al. | |
| 5,124,299 A | 6/1992 | Waller | |
| 5,171,921 A | 12/1992 | Gaffney et al. | |
| 5,173,461 A | 12/1992 | Absil et al. | |
| 5,178,748 A | 1/1993 | Casci et al. | |
| 5,210,356 A | 5/1993 | Shamshoum et al. | |
| 5,227,558 A | 7/1993 | Shamshoum et al. | |
| 5,231,064 A | 7/1993 | Absil et al. | |
| 5,233,102 A | 8/1993 | Butt et al. | |
| 5,244,852 A * | 9/1993 | Lachman et al. | 502/66 |
| 5,246,688 A | 9/1993 | Faust et al. | |
| 5,248,841 A | 9/1993 | Young | |
| 5,254,767 A | 10/1993 | Dwyer | |
| 5,254,770 A | 10/1993 | Olson et al. | |
| 5,294,332 A | 3/1994 | Klotz | |
| 5,294,578 A | 3/1994 | Ho et al. | |
| 5,315,033 A | 5/1994 | Butt et al. | |
| 5,318,696 A | 6/1994 | Kowalski | |
| 5,321,183 A | 6/1994 | Chang et al. | |
| 5,330,732 A | 7/1994 | Ishibashi et al. | |
| 5,336,478 A | 8/1994 | Dwyer et al. | |
| 5,336,824 A | 8/1994 | Shamshoum et al. | |
| 5,345,021 A | 9/1994 | Casci et al. | |
| 5,348,643 A | 9/1994 | Absil et al. | |
| 5,349,113 A | 9/1994 | Chang et al. | |
| 5,365,003 A | 11/1994 | Chang et al. | |
| 5,366,948 A | 11/1994 | Absil et al. | |
| 5,367,100 A | 11/1994 | Gongwei et al. | |
| 5,371,307 A | 12/1994 | Guth et al. | |
| 5,378,670 A | 1/1995 | Kumar | |
| 5,380,690 A | 1/1995 | Zhicheng et al. | |
| 5,385,718 A | 1/1995 | Casci et al. | |
| 5,387,732 A | 2/1995 | Shamshoum et al. | |
| 5,399,336 A | 3/1995 | Guth et al. | |
| 5,430,212 A | 7/1995 | Butt et al. | |
| 5,430,213 A | 7/1995 | Hendriksen et al. | |
| 5,446,234 A | 8/1995 | Casci et al. | |
| 5,455,213 A | 10/1995 | Chang et al. | |
| 5,456,821 A | 10/1995 | Absil et al. | |
| 5,464,799 A | 11/1995 | Casci et al. | |
| 5,475,179 A | 12/1995 | Chang et al. | |
| 5,498,814 A | 3/1996 | Chang et al. | |
| 5,503,818 A | 4/1996 | Nicolaides | |
| 5,512,260 A | 4/1996 | Kiliany et al. | |
| 5,516,736 A | 5/1996 | Chang et al. | |
| 5,523,510 A | 6/1996 | Pellet et al. | |
| 5,529,964 A | 6/1996 | Weitkamp et al. | |
| 5,534,239 A | 7/1996 | Fajula et al. | |
| 5,536,894 A | 7/1996 | Degnan et al. | |
| 5,541,146 A | 7/1996 | Chang et al. | |
| 5,561,095 A | 10/1996 | Chen et al. | |
| 5,563,310 A | 10/1996 | Chang et al. | |
| 5,569,805 A | 10/1996 | Beck et al. | |
| 5,571,768 A | 11/1996 | Chang et al. | |
| 5,573,746 A | 11/1996 | Chen | |
| 5,576,256 A | 11/1996 | Monque et al. | |
| 5,607,888 A | 3/1997 | Chang et al. | |
| 5,607,890 A | 3/1997 | Chen et al. | |
| 5,646,314 A | 7/1997 | Crocco et al. | |
| 5,648,580 A | 7/1997 | Chen et al. | |
| 5,658,454 A | 8/1997 | Absil et al. | |
| 5,675,047 A | 10/1997 | Beck et al. | |
| 5,689,024 A | 11/1997 | Schmitt | |
| 5,698,756 A | 12/1997 | Beck et al. | |
| 5,726,114 A | 3/1998 | Chang et al. | |
| 5,780,563 A | 7/1998 | Chen et al. | |
| 5,789,335 A | 8/1998 | Chen et al. | |
| 5,811,613 A | 9/1998 | Bhat et al. | |
| 5,833,840 A | 11/1998 | Absil et al. | |
| 5,847,255 A | 12/1998 | Ghosh et al. | |
| 5,856,603 A | 1/1999 | Rekker et al. | |
| 5,902,919 A | 5/1999 | Chen et al. | |
| 5,905,051 A | 5/1999 | Wu et al. | |
| 5,907,073 A | 5/1999 | Ghosh | |
| 5,907,074 A * | 5/1999 | Wu et al. | 585/489 |
| 5,922,922 A | 7/1999 | Harris et al. | |
| 5,925,586 A | 7/1999 | Sun | |
| 5,939,597 A | 8/1999 | Dessau et al. | |
| 5,951,963 A | 9/1999 | He et al. | |
| 5,952,535 A | 9/1999 | King et al. | |
| 5,955,641 A | 9/1999 | Chen et al. | |
| 5,968,463 A | 10/1999 | Shelef et al. | |
| 5,990,031 A | 11/1999 | Ghosh | |
| 5,994,550 A * | 11/1999 | Chitnis et al. | 546/251 |
| 5,994,603 A | 11/1999 | Mohr et al. | |
| 6,034,283 A | 3/2000 | Ban et al. | |
| 6,040,257 A | 3/2000 | Drake et al. | |
| 6,046,128 A | 4/2000 | Kisen et al. | |
| 6,047,544 A | 4/2000 | Yamamoto et al. | |
| 6,048,816 A | 4/2000 | Brown et al. | |
| 6,057,485 A | 5/2000 | Merrill et al. | |
| 6,060,633 A | 5/2000 | Chen et al. | |
| 6,074,975 A | 6/2000 | Yao et al. | |
| 6,080,303 A | 6/2000 | Cao et al. | |
| 6,080,698 A | 6/2000 | Zhang et al. | |
| 6,083,865 A | 7/2000 | Drake et al. | |
| 6,090,274 A | 7/2000 | Wu et al. | |
| 6,090,991 A | 7/2000 | Butler et al. | |
| 6,096,938 A | 8/2000 | Ghosh | |
| 6,100,437 A | 8/2000 | Koehl et al. | |
| 6,124,227 A | 9/2000 | Yao et al. | |
| 6,150,293 A | 11/2000 | Verduijn et al. | |
| 6,156,949 A | 12/2000 | Brown et al. | |
| 6,160,191 A | 12/2000 | Smith et al. | |
| 6,187,982 B1 | 2/2001 | Beck et al. | |
| 6,211,104 B1 | 4/2001 | Shi et al. | |
| 6,217,748 B1 | 4/2001 | Hatanaka et al. | |
| 6,222,084 B1 | 4/2001 | Ghosh et al. | |
| 6,251,263 B1 | 6/2001 | Hatanaka et al. | |
| 6,268,305 B1 | 7/2001 | Butler et al. | |
| 6,294,493 B1 | 9/2001 | Strohmaier et al. | |
| 6,300,535 B1 | 10/2001 | van den Berge et al. | |
| 6,306,790 B1 | 10/2001 | Rodriguez et al. | |
| 6,319,484 B1 | 11/2001 | Shore et al. | |
| 6,342,153 B1 | 1/2002 | Guan et al. | |
| 6,346,190 B1 | 2/2002 | Khare | |
| 6,388,156 B1 | 5/2002 | Ou et al. | |
| 6,395,664 B1 | 5/2002 | Boehner et al. | |
| 6,399,530 B1 | 6/2002 | Chen et al. | |
| 6,417,421 B1 | 7/2002 | Yao | |
| 6,423,879 B1 | 7/2002 | Brown et al. | |
| 6,444,610 B1 | 9/2002 | Yamamoto | |
| 6,459,006 B1 | 10/2002 | Ou et al. | |
| 6,469,095 B1 | 10/2002 | Gareiss et al. | |
| 6,503,862 B1 | 1/2003 | Yamamoto | |
| 6,504,072 B1 | 1/2003 | Brown et al. | |
| 6,504,074 B2 | 1/2003 | Berduijn et al. | |
| 6,506,954 B1 | 1/2003 | Brown et al. | |
| 6,518,213 B1 | 2/2003 | Yamamoto et al. | |
| 6,548,725 B2 | 4/2003 | Froment et al. | |
| 6,566,293 B1 | 5/2003 | Vogt et al. | |
| 6,589,901 B2 | 7/2003 | Yamamoto | |

(56) References Cited

U.S. PATENT DOCUMENTS

| | | |
|---|---|---|
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 6,864,399 B2 | 3/2005 | Merrill et al. |
| 6,943,131 B1 * | 9/2005 | Ghosh et al. .......... 502/71 |
| 7,060,644 B2 * | 6/2006 | Ghosh et al. .......... 502/60 |
| 7,060,864 B2 * | 6/2006 | Ghosh et al. .......... 585/467 |
| 7,084,318 B2 | 8/2006 | Ghosh et al. |
| 7,105,713 B2 | 9/2006 | Ghosh et al. |
| 7,119,239 B2 | 10/2006 | Johnson et al. |
| 7,176,339 B2 | 2/2007 | Iaccino et al. |
| 7,186,873 B2 | 3/2007 | Feng et al. |
| 7,196,237 B2 | 3/2007 | Ghosh et al. |
| 7,232,516 B2 | 6/2007 | Sughure, II et al. |
| 7,244,869 B2 * | 7/2007 | Ghosh et al. .......... 585/467 |
| 7,279,608 B2 * | 10/2007 | Ghosh et al. .......... 585/467 |
| 7,285,511 B2 * | 10/2007 | Ghosh et al. .......... 502/64 |
| 7,304,194 B2 | 12/2007 | Ghosh et al. |
| 7,363,410 B2 | 4/2008 | Bian et al. |
| 7,368,410 B2 * | 5/2008 | Ghosh et al. .......... 502/63 |
| 7,396,967 B2 | 7/2008 | Iaccino et al. |
| 7,399,727 B2 * | 7/2008 | Ghosh et al. .......... 502/77 |
| 7,446,069 B2 | 11/2008 | Ghosh et al. |
| 7,507,685 B2 * | 3/2009 | Ghosh et al. .......... 502/63 |
| 7,560,608 B2 * | 7/2009 | Ghosh et al. .......... 585/466 |
| 7,576,026 B2 * | 8/2009 | Ghosh et al. .......... 502/77 |
| 7,662,737 B2 * | 2/2010 | Ghosh et al. .......... 502/63 |
| 7,674,942 B2 * | 3/2010 | Ghosh et al. .......... 585/446 |
| 2003/0004383 A1 | 1/2003 | Brown et al. |
| 2003/0121827 A1 | 7/2003 | van den Berge et al. |
| 2003/0127360 A1 | 7/2003 | van den Berge et al. |
| 2004/0004023 A1 | 1/2004 | Sughrue, II et al. |
| 2004/0087822 A1 | 5/2004 | Buchanan et al. |
| 2004/0158111 A1 | 8/2004 | Johnson et al. |
| 2004/0262200 A1 | 12/2004 | Sughure, II et al. |
| 2005/0020435 A1 | 1/2005 | Beck et al. |
| 2005/0070749 A1 | 3/2005 | Ghosh et al. |
| 2005/0075524 A1 | 4/2005 | Feng et al. |
| 2005/0143613 A1 | 6/2005 | Dakka et al. |
| 2005/0194289 A1 | 9/2005 | Overbeek et al. |
| 2005/0202956 A1 | 9/2005 | Sterte et al. |
| 2006/0151358 A1 | 7/2006 | Brown et al. |
| 2007/0015658 A1 | 1/2007 | Turaga et al. |
| 2007/0225156 A1 | 9/2007 | Sughure, II et al. |
| 2008/0058564 A1 | 3/2008 | Iaccino et al. |
| 2008/0176736 A1 | 7/2008 | Ghosh et al. |
| 2009/0253949 A1 | 10/2009 | Ghosh et al. |
| 2010/0168489 A1 | 7/2010 | Ghosh et al. |

OTHER PUBLICATIONS

F.M. Bautista, et al., Continuous Flow Toluene Methylation Over AlPO4 and AlPO4—Al2O3 Catalysts, Catalysis Letters, 1994, pp. 159-167, vol. 26.

International Search Report for International Application No. PCT/US2009/05613; International Filing Date Oct. 14, 2009, Date of Mailing Dec. 11, 2009; 2 pages.

Written Opinion of International Application No. PCT/US2009/05613; International Filing Date Oct. 14, 2009, Date of Mailing Dec. 11, 2009; 5 pages.

* cited by examiner

STABLE SHAPE-SELECTIVE CATALYST FOR AROMATIC ALKYLATION AND METHODS OF USING AND PREPARING

TECHNICAL FIELD

The invention relates generally to the alkylation of aromatic compounds and catalysts used for such reactions.

BACKGROUND

Aromatic compounds may be alkylated to form different alkylated aromatic products. One that has particular value is para-xylene. Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite catalyst. In particular, ZSM-5 zeolite, zeolite Beta and silicoaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 zeolite catalysts giving xylene products containing significantly greater amounts of p-xylene than the thermodynamic concentration.

Unfortunately, there are a number of technical hurdles for toluene methylation to be commercially successful. These include fast catalyst deactivation, low methanol selectivity, and so on. Most of the catalysts, if not all, for toluene methylation show fast catalyst deactivation. Typically, toluene conversion declines with time on stream due to rapid coke formation on the catalyst. The catalyst deactivation is one of the most difficult technical hurdles to overcome for commercial use of toluene methylation.

The present invention is directed to a catalyst and a method of preparation of a catalyst that has shape selective properties and that also has increased catalyst stability when used in aromatic alkylation reactions, such a toluene methylation.

BRIEF DESCRIPTION OF THE DRAWINGS

For a more complete understanding of the present invention, reference is now made to the following descriptions taken in conjunction with the accompanying figures, in which.

DETAILED DESCRIPTION

Zeolites are aluminosilicate materials having microporous structures. They may be naturally occurring or synthesized. Zeolites are commonly used as catalysts in a variety of different hydrocarbon conversion reactions such as isomerization and alkylation reactions. Among these is the alkylation of aromatic compounds.

The ZSM-5 zeolite is one of the most versatile zeolites used for catalyst in aromatic alkylation. Specific reference is made to the use of a ZSM-5 zeolite that has been modified in accordance with the invention for use in toluene methylation, for which the modified zeolite is particularly well suited. It will be apparent to those skilled in the art, however, that the zeolite catalysts described herein may have application for use in other types of reactions, such as transalkylation and other aromatic alkylation reactions. In particular, the catalyst of the invention may have application to reactions to provide increased selectivity for para-isomers in mixed dialkylated aromatic products.

The ZSM-5 zeolite is a porous material containing intersecting two-dimensional pore structure with 10-membered oxygen rings. Zeolite materials with such 10-membered oxygen ring pore structures are often classified as medium-pore zeolites. Such medium-pore zeolites typically have pore diameters ranging from 5.0 Å to 7.0 Å. The ZSM-5 zeolite is a medium pore-size zeolite with a pore diameter of from about 5.1 to about 5.6 Å.

Although specific reference and emphasis is made with respect to ZSM-5 zeolite, other zeolites may be treated and formed using the techniques described herein as well. One skilled in the art will therefore readily appreciate that other zeolite materials besides ZSM-5 zeolite may provide similar properties to those of the ZSM-5 zeolite materials described, such as mordenite, omega, etc. These may be medium pore zeolites as well.

The ZSM-5 zeolite catalysts and their preparation are described in U.S. Pat. No. 3,702,886, which is herein incorporated by reference. The starting ZSM-5 may be an $NH_4^+$ or $H^+$ form and may contain traces of other cations. In the present invention, the ZSM-5 zeolite catalyst may have a silica/alumina molar ratio of from about 30 or lower to about 1000 or higher prior to modification, more particularly, the silica/alumina molar ratio may be from about 30, 50, 80, 100, 200, 250, 300, 400, 500 to about 1000 or more, including any and all data points within such range and the end points of the such range.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

To provide para-selective properties to the ZSM-5 zeolite or other zeolites, the zeolite is modified by treating it with phosphorus-containing compounds. Such phosphorus-containing compounds may include, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4)_2HPO_4$) may be used as the phosphorus-containing compound to provide a catalyst for aromatic alkylation or toluene methylation with shape selective properties to provide increased para-selectivity. Such modified catalysts may contain phosphorus (P) in an amount of from about 0.01 wt % to about 15 wt % by total weight of the catalyst.

The phosphorus treatment may be carried out by various techniques. This may include slurry evaporation, wet incipient and spray-dry methods. In slurry evaporation, the phosphorus may be incorporated into the catalyst by preparing a slurry of the zeolite and an aqueous solution of the phosphorus compound. Heating of the slurry may be used to facilitate treatment of the zeolite catalyst and to evaporate liquids. Heating of the slurry to temperatures of from about 25° C. or more, with from about 70° C. to about 100° C. may be suitable in most instances. The slurry may also be stirred or agitated during this step to ensure uniform treatment. The evaporation of the liquid from the zeolite slurry can be alternatively achieved by using a spray-dry technique which is well known in the art.

In the wet incipient method, an aqueous solution of the phosphorus compound is added, such as by spraying, to dry zeolite without forming a slurry. The dry zeolite, which may be initially in the form of a powder, may be mixed with the phosphorus compound or its aqueous solution. If necessary, water may be added to the mixture of zeolite powder and phosphorus containing compound or its solution to facilitate interaction between them. The phosphorus treated zeolite is then calcined using a temperature profile with a maximum temperature of from about 400° C. to about 700° C. In some embodiments, the P-treated zeolite may be heated at a temperature of about 300° C. or higher prior to binding and then the zeolite is bound with a suitable binder, as described in U.S. Pat. No. 7,368,410, which is herein incorporated by reference.

The phosphorus treated zeolite after calcination is combined with a binder material to form catalyst with a particular shape, for example, 1/16-inch diameter cylindrical shaped extruded catalyst. The binder materials may include inorganic oxide materials. In particular, a binder of an aluminum-containing material, such as alumina, clay, aluminum phosphate, silica-alumina or other-aluminum containing material, or their combinations, may be particularly useful. The bound catalyst may contain from about 1 wt % to about 99 wt % of binder material by total weight of the catalyst. In some applications the binder may be present in an amount of from about 10 wt % to about 50 wt % binder by total weight of catalyst.

Even without a binder the phosphorus treated zeolite (prior to calcination as described above) can also be formed into a particular shape and size as catalyst, for example, 1/16-inch diameter cylindrical shaped extrudates. Such catalyst may be described as "self-bound" catalyst.

The formed catalyst (either self-bound or bound with binder such as alumina) may then be calcined or heated at a temperature of about 400° C. or higher, more particularly at a temperature from about 450° C. to about 700° C. Such heating may be carried out for 0.5 hours or more.

In order to provide increased catalyst activity or stability, the bound phosphorus-treated zeolite includes a hydrogenating metal. The hydrogenating metal may be any of the group VIIIA transition metals and may include nickel, palladium and platinum, as well as other metals. Nickel is particularly well suited as the hydrogenating metal. The hydrogenating metal may be present in an amount of from about 0.01 weight % to about 5.0 weight %, more particularly, from about 0.03 weight % to about 2.0 weight % of the total weight of zeolite catalyst. The hydrogenating metal may be added to the catalyst as hydrogenating metal salt or other compound that readily dissolves in water.

Unexpectedly, the presence of a hydrogenating metal in a bound phosphorus-treated ZSM-5 zeolite catalysts has an impact on the activity of the final catalyst. A hydrogenating metal deposited on the bound phosphorus-treated zeolite provides increased activity. Deposition of the hydrogenating metal may be carried out by immersing the bound phosphorus-treated zeolite catalyst in an aqueous solution containing the hydrogenating metal. The temperature of the solution may be maintained at room temperature or a temperature below the boiling point of the solution. After a period of 5 min or more, the liquid is separated from the solid. This is done through decantation or filtration or other non-evaporative separation techniques for separating liquids from solids. As used herein, the term or expression "separation," "separating" or similar expressions as it is applied to the separation of the liquids and solids upon the treatment of the zeolite with an aqueous solution of a hydrogenating metal is meant to exclude evaporation of liquids from the solids. As is demonstrated in the examples, treatment of self-bound P/ZSM-5 catalyst with the hydrogenating metal solution did not result in a catalyst exhibiting the increased catalytic activity.

The method of treatment of the bound P/ZSM-5 catalyst with hydrogenating metal has an added impact on catalyst activity or stability as well. As demonstrated in the examples, the separation of liquid by filtration or decantation technique after treating the bound zeolite catalyst with solution containing hydrogenating metal resulted in a catalyst with further increased activity or stability than the commonly used impregnation technique where the liquid is evaporated to dryness. See, for example, Table 7: Catalyst G v. Catalyst E.

After treatment with the hydrogenating metal, the treated catalyst may be calcined at a temperature from about 400° C. to about 600° C. in an environment containing oxygen, typically air. The hydrogenating metal in the catalyst after such calcinations may be present in the oxide form, for example, Ni as NiO.

The hydrogenating metal loaded zeolite catalyst may be further pretreated prior to use in alkylation or other reactions to reduce or to lower the oxidation state of the hydrogenating metal in a reducing environment. Such treatment includes contacting the catalyst with a reducing gas at an elevated temperature. The reducing gas may be hydrogen ($H_2$) or a hydrogen-containing gas, such as a mixture of hydrogen and nitrogen ($N_2$) or light alkane(s). The catalyst is contacted with the reducing gas, which may be mixed with an inert carrier gas, such as nitrogen at an initial starting temperature. The temperature may be slowly ramped up during the pretreatment, with the initial starting temperature being from about 100 to about 200° C., and which may be increased at a rate of from about 0.2 to about 10.0° C./min to the final pretreatment temperature. The final pretreatment temperature may be from about 350 to about 600° C., more particularly from about 400 to about 550° C. The pretreatment may be carried out from about 0.5 to 10 hours or more, more particularly from 1 to 9 hours, and still more particularly from about 2 to 7 hours.

Based on temperature programmed reduction profile data on NiO or the $Ni^{2+}$ containing zeolite catalyst, it is believed that the above described catalyst pretreatment may cause reduction of $Ni^{2+}$ to $Ni^+$ and $Ni^0$. The hydrogenating metal ions to an oxidation state of less than 1 may be useful in retarding the coke formation during the alkylation reactions, and thus facilitate increasing the catalyst stability.

After reducing, the hydrogenating metal containing zeolite catalyst may also be steamed prior to use for the catalytic reactions. The catalyst may be steamed at a temperature of 300° C. or lower before using the catalyst in any reaction. The steaming can be carried out in-situ or ex-situ of the reactor. In some embodiments, the catalyst is steamed at mild temperatures. Methods for steaming at mild temperatures that are useful in the present invention are described in U.S. Pat. No. 7,304,194, which is herein incorporated by reference.

After reducing and any steaming, the catalyst may be contacted with an appropriate feed under alkylation reaction conditions to carry out the aromatic alkylation. Examples of alkylation reactions for which the invention has application include toluene alkylation with an alkylating agent such as methanol. Other examples may include gas phase toluene disproportionation in the presence of hydrogen producing benzene and mixed-xylenes. While the invention has application to many aromatic alkylation reactions, it is particularly well suited for toluene methylation to produce para-xylene using ZSM-5 zeolite catalyst. Although much of the description herein may be directed to such toluene methylation, it will be readily understood by those skilled in the art that it is not solely limited to such use.

The hydrogenating metal containing zeolite catalyst may be contacted with an appropriate feed of an aromatic hydrocarbon and an alkylating agent under alkylation reaction conditions to carry out aromatic alkylation. In aromatic alkylation an "alkylation feed" feed may be used. A gas cofeed may also be used. The cofeed gas may include hydrogen or an inert gas. As used herein, the expression "alklyation feed" is meant to encompass the aromatic compound and the alkylating agent. As used herein with respect to toluene methylation, the expression "methylation feed" is meant to encompass the feed of toluene and methanol.

In addition to any cofeed gas, water that may be in the form of steam, may also be introduced into the reactor as cofeed along with the alkylation feed. The water or steam used for the alkylation or methylation reaction may be introduced, with or without hydrogen or inert gas as cofeed, with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed in aromatic alkylation is described in U.S. Pat. No. 7,060,864, which is hereby incorporated by reference.

The reactor pressure for toluene methylation or other aromatic alkylation may vary, but typically ranges from about 10 to about 1000 psig. Reactor temperatures may vary, but typically range from about 400 to about 700° C. Upon introduction of feed into the reactor, the catalyst bed temperature may be adjusted to a selected reaction temperature to effect a desired conversion. The temperature may be increased gradually at a rate of from about 0.1° C./min to about 10° C./min to provide the desired final reactor temperature. As used in the examples, reactor temperature refers to the temperature as measured at the inlet of catalyst bed of the reactor.

The reaction may be carried out in a variety of different reactors that are commonly used for carrying out aromatic alkylation reactions. Single or multiple reactors in series and/or parallel may be suitable for carrying out the aromatic alkylation or toluene methylation reactions.

As used herein, catalytic activity can be expressed as the % moles of the hydrocarbon or reactant converted with respect to the moles of hydrocarbon or reactant fed. In toluene methylation where toluene is converted to xylenes, the catalytic activity may be measured by the toluene converted with respect to the moles of toluene fed and can be defined by the following formulas:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for mixed xylenes may be expressed as:

$$\text{Mole \% Mixed Xylene Selectivity} = [X_{tx}/(T_i - T_o)] \times 100 \quad (3)$$

where, $X_{tx}$ is the number of moles of total or mixed (o-, m- or p-) xylenes in the product. As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.
As used herein, methanol conversion may be expressed as:

$$\text{Mole \% Methanol Conversion} = [(M_i - M_o)/M_i] \times 100 \quad (5)$$

where, $M_i$ is the number of moles of methanol fed and $M_o$ is the number of moles methanol unreacted.
As used herein, methanol selectivity for toluene methylation may be expressed as:

$$\text{Mole \% Methanol Selectivity} = [X_{tx}/(M_i - M_o)] \times 100 \quad (6)$$

where, $X_{tx}$ is the number of moles of mixed (o-, m- or p-) xylenes, $M_i$ is the number of moles of methanol fed and $M_o$ is the number of moles of unreacted methanol.

The following examples better serve to illustrate the invention.

EXAMPLES

Example 1

Comparative Catalyst A

A $NH_4$-ZSM-5 zeolite powder having a $SiO_2/Al_2O_3$ mole ratio of between 250 and 300 was treated with $H_3PO_4$ and then was calcined at a temperature of about 530° C. The phosphorus treated ZSM-5 zeolite was crushed into fine powder and was then combined with about 20% by weight of alumina binder and extruded into 1/16-inch diameter cylindrical shaped catalyst extrudates. The bound zeolite was then calcined or heated to a temperature of 530° C. The powdered phosphorus treated ZSM-5 (P/ZSM-5) and the alumina bound P/ZSM-5 catalyst (Catalyst A) were analyzed for $Na_2O$, $P_2O_5$, $SiO_2$ and $Al_2O_3$ by X-ray fluorescence (XRF), and for BET surface area and total pore volume by $N_2$ adsorption. The results are shown in Table 1 below.

TABLE 1

| | Elemental Analysis, wt % | | | | $N_2$ Adsorption | |
|---|---|---|---|---|---|---|
| | $Na_2O$ | $P_2O_5$ | $SiO_2$ | $Al_2O_3$ | SA, $m^2/g$ | $N_2$ PV, cc/g |
| Powdered P/ZSM-5 | <0.04 | 21.6 | 79.2 | 0.5 | 211 | 0.13 |
| Catalyst A | <0.04 | 17.2 | 63.4 | 20.4 | 243 | 0.17 |

Catalyst A, described above, was tested for toluene methylation reaction in a fixed bed, continuous flow type reactor. A catalyst charge of 5.4 ml (catalyst size: 20-40 mesh) was loaded in the reactor. The catalyst was dried by slowly raising the catalyst bed temperature (about 5° C./min) to 150° C. under hydrogen flow (200 cc/min) for about one hour. The catalyst was further heated at 480° C. for 3 hours under $H_2$ flow (same flow rate). The catalyst was steamed by introducing water vapor (2.2 mmole/min) with a carrier gas of $H_2$ (459 cc/min) at 200° C. overnight. A premixed toluene and methanol feed (molar ratio 4.5) was added to the reactor at 200° C. The liquid hourly space velocity (LHSV) [based on methylation feed (toluene+methanol)] was maintained at about 2 $hr^{-1}$ and a cofeed of $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor inlet pressure was about 20 psig. The catalyst bed inlet temperature was increased to 450° C. and then adjusted to 485° C., at which toluene conversion was about 11.4 mole %. Reactor streams were analyzed to calculate conversion and selectivity.

Figure 1:
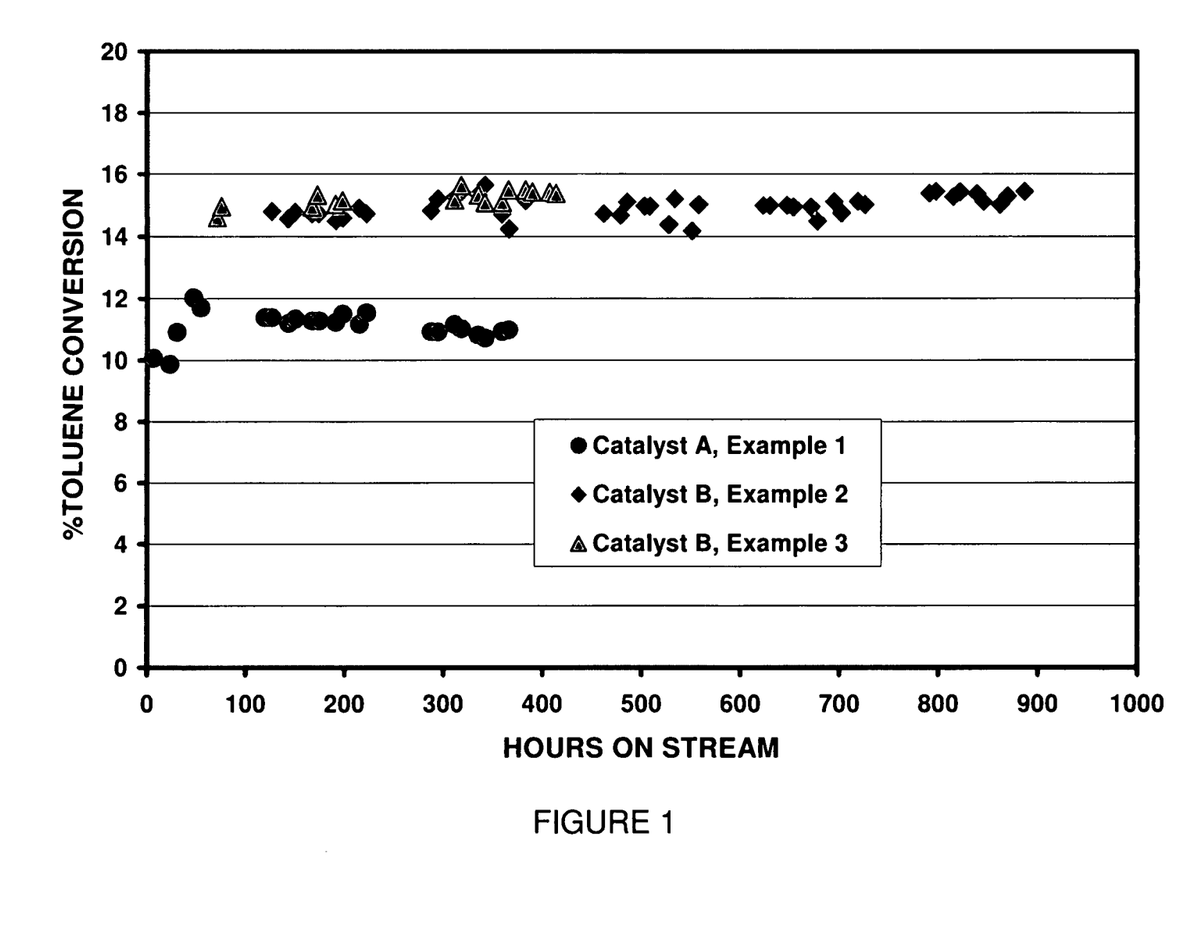
FIG. 1 shows a plot of toluene conversion over time for toluene methylation reactions using Catalyst A (without metal) and Catalyst B (containing nickel) from Examples 1-3.

FIG. 1 shows toluene conversion for Catalyst A at different times on stream during a test period of about 365 hour. The reactor temperature was kept unchanged at catalyst bed inlet temperature of about 485° C. and average bed temperature of about 494° C. Toluene conversion was found to decline with time on stream at a constant catalyst bed inlet temperature. This decline in conversion per unit time is the deactivation rate and it is estimated to be −0.065% per 24 hours. Table 2 shows toluene conversion, methanol conversion, toluene selectivity for mixed xylenes, para-xylene selectivity and methanol selectivity to mixed xylenes for Catalyst A.

Example 2

Catalyst B

Nickel was incorporated with the alumina bound P/ZSM-5 zeolite catalyst (Catalyst A) from Example 1 to form Catalyst B. Weighted 0.737 g of nickel hexahydrate was dissolved in 100 ml deionized water in a flask and 30.03 g extrudates of Catalyst A was immersed in the nickel salt solution in the flask which was then shaken for 5 minutes and was aged at 60° C. overnight. Catalyst A was then separated by decanting the liquid. The nickel-treated zeolite was then calcined at a maximum temperature of about 530° C. for 10 hours. The nickel content of the catalyst was 0.07 wt % by total weight as measured by XRF analysis. Catalyst preparation and analysis for Catalyst B are summarized in Table 3.

Catalyst B, described above, was tested for toluene methylation reaction in a fixed bed, continuous flow type reactor. A catalyst charge of 5.4 ml (catalyst size: 20-40 mesh) was loaded in the reactor. The catalyst was dried by slowly raising the catalyst bed temperature (about 5° C./min) to 150° C. under hydrogen flow (200 cc/min) for at least one hour. The catalyst was further heated (reduced) at 430° C. for 3 hours under $H_2$ flow (same flow rate). The catalyst was steamed by introducing water vapor (2.2 mmole/min) with a carrier gas of $H_2$ (459 cc/min) at 200° C. overnight. A premixed toluene and methanol feed (molar ratio 4.5) was added to the reactor at 200° C. The liquid hourly space velocity (LHSV) [based on methylation feed (toluene+methanol)] was maintained at about 2 $hr^{-1}$ and a cofeed of $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig and the catalyst bed inlet temperature was increased to 450° C. and then adjusted to 495° C. at which toluene conversion was about 15.4 mole %. Reactor streams were analyzed to calculate conversion and selectivity.

TABLE 3

| Catalyst | (Extruded) Base Catalyst, g | Ni Salt, g | Water, ml | Aging Temp | Liquid Removal, Calcination | Wt % Ni by XRF |
|---|---|---|---|---|---|---|
| Catalyst A | Base Catalyst | N/A | N/A | N/A | N/A | N/A |
| Catalyst B | 30.025 | 0.737 | 100 | 60° C. | Decanted & Calcined at 530° C. | 0.07 |
| Catalyst C | 30.107 | 0.247 | 100 | 60° C. | Decanted & Calcined at 530° C. | 0.03 |
| Catalyst D | 30.154 | 0.247 | 100 | 60° C. | Decanted & Calcined at 530° C. | 0.04 |
| Catalyst E | 30.049 | 1.106 | 100 | 60° C. | Decanted & Calcined at 530° C. | 0.09 |
| Catalyst F | 30.070 | 1.477 | 100 | 60° C. | Decanted & Calcined at 530° C. | 0.15 |
| Catalyst G | 30.367 | 0.153 | 100 | 90° C. | Evaporated, Calcined at 530° C. | 0.10 |

Base Catalyst = Alumina Bound P/ZSM-5 Extruded Catalyst

FIG. 1 shows toluene conversion for Catalyst B, which was prereduced at 430° C., at different times on stream during a test period of about 893 hours. The reactor temperature was kept unchanged at a catalyst bed inlet temperature of about 487° C. and average bed temperature of about 496° C. The toluene conversion remained unchanged or somewhat increased during the test period at constant temperature showing catalyst stability. In other words, catalyst deactivation was not observed for Catalyst B during the 893 hour test run. The carbon (C) content on the spent catalyst was 2.3 wt %. Table 2 shows toluene conversion, methanol conversion, toluene selectivity for mixed xylenes, para-xylene selectivity and methanol selectivity to mixed xylenes for Catalyst B.

Example 3

As in Example 2, Catalyst B was employed in toluene methylation. The reactor, catalyst loading, drying and steaming conditions were the same as in Example 2, except the catalyst was heated at a pre-reduction temperature of about 480° C. instead of 430° C. under $H_2$ flow prior to steaming.

FIG. 1 shows toluene conversion at different times on stream during test period of 414 hours. The reactor temperature was kept unchanged at a catalyst bed inlet temperature of about 485° C. and the average bed temperature was about 493° C. at which toluene conversion was about 15.4 mole %. The toluene conversion remained unchanged or somewhat increased during the test period at constant temperature showing catalyst stability. That is, the catalyst deactivation was not observed for Catalyst B during the 414 hour test period. The carbon (C) content on the spent catalyst was 3.4 wt %. Table 2 shows toluene conversion, methanol conversion, toluene selectivity for mixed xylenes, para-xylene selectivity and methanol selectivity to mixed xylenes for Catalyst B that was prereduced at 480° C.

Example 4-7

Catalysts C-F

In addition to Catalyst B, several nickel-loaded catalysts with different nickel contents were tested in toluene methylation reactions to examine the effects of Ni content on catalyst activity, selectivity and stability. Ni loaded catalysts C, D, E and F were made using base Catalyst A and the same procedure as described for Catalyst B above. Table 3 shows the amounts of base catalyst, nickel salt, amount of water used, aging temperature and nickel content (measured by XRF) on the final catalysts. The Ni contents in the catalysts varied from 0.03 wt % to about 0.15 wt %.

Figure 2:
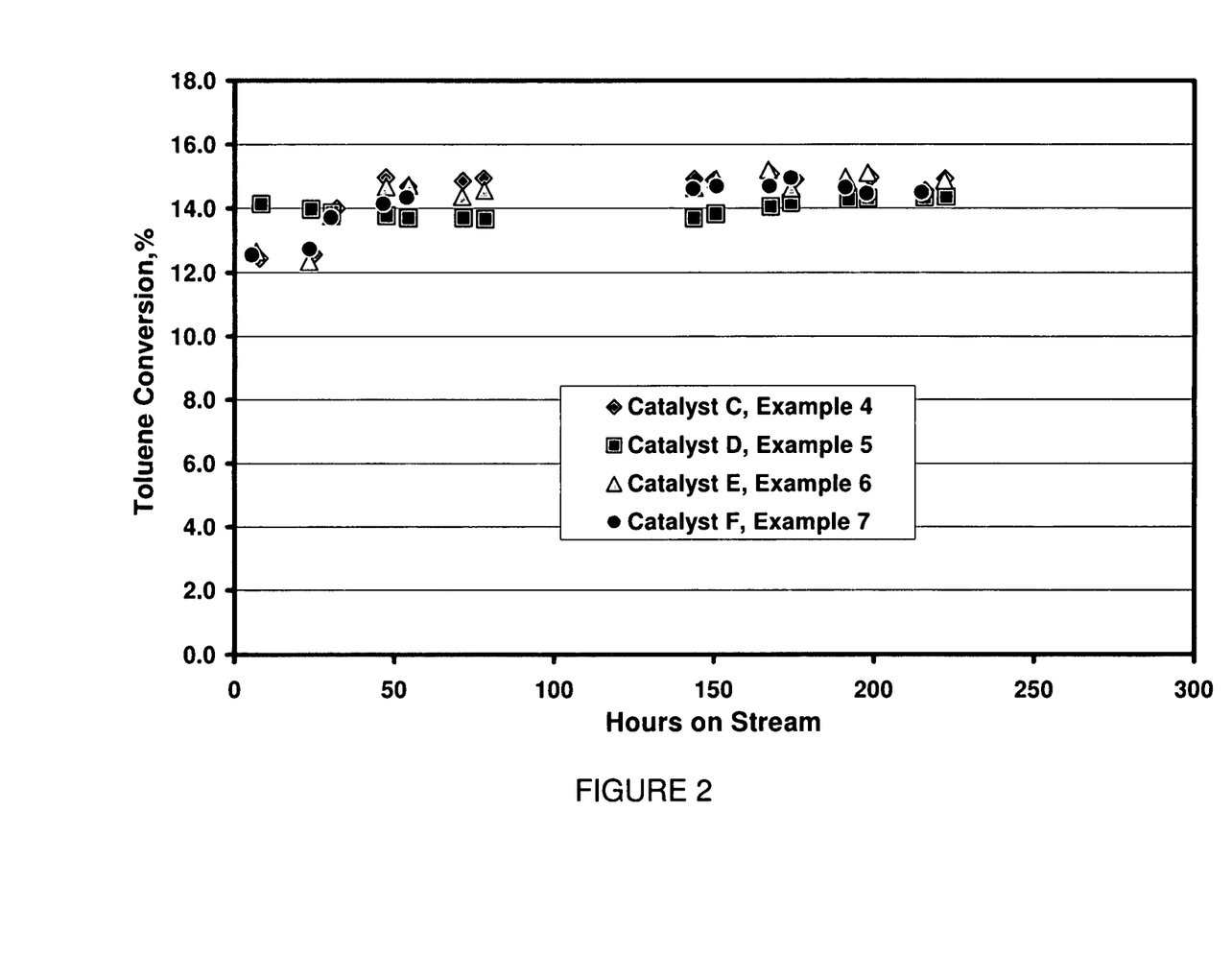
FIG. 2 shows a plot of toluene conversion over time for toluene methylation reactions using Catalysts C-F (containing different amounts of nickel) from Examples 4-7.

Catalysts C, D, E and F were tested in toluene methylation reactions. Catalyst loading, predrying, steaming and testing conditions were the same as described for Example 3. FIG. 2 shows toluene conversions at different times on stream over Catalysts C, D, E and F. Table 2 summarizes toluene conversion, methanol conversion, toluene selectivity for mixed xylenes, para-xylene selectivity and methanol selectivity to mixed xylenes for Catalysts C, D, E and F.

Catalysts B, C, D, E and F showed an increased catalyst activity showing higher toluene conversion compared to Catalyst A (Table 2, Examples 1-7).

Example 8

Catalyst G

In this example, an impregnation technique was used to form a Ni loaded catalyst (Catalyst G). In this technique, nickel was incorporated with the alumina bound P/ZSM-5 zeolite catalyst from Example 1 (Catalyst A). Nickel hexahydrate in an amount of 0.153 g was dissolved in 100 ml deionized water. The nickel salt solution was added to 30.4 g of the extruded Catalyst A in a ceramic bowl and aged at 90° C. overnight. Most of the liquid was evaporated and further evaporation continued during calcination at 530° C.

Catalyst G was then used in toluene methylation, as in the previous examples. A catalyst charge of 5.4 ml (catalyst size: 20-40 mesh) was loaded in the reactor. The catalyst was dried by slowly raising the catalyst bed temperature (about 5° C./min) to 150° C. under hydrogen flow (200 cc/min) for at least one hour. The catalyst was further heated (reduced) at 480° C. for 3 hours under $H_2$ flow (same flow rate). The catalyst was steamed by introducing water vapor (2.2 mmole/min) with a carrier gas of $H_2$ (459 cc/min) at 200° C. overnight. A premixed toluene and methanol feed (molar ratio 4.5) was added to the reactor at 200° C. The liquid hourly space velocity (LHSV) [based on methylation feed (toluene+methanol)] was maintained at about 2 $hr^{-1}$ and a cofeed of $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig and the catalyst bed inlet temperature was increased to 450° C. and then adjusted to about 485° C. (average catalyst bed temperature 498° C.). Reactor streams were analyzed to calculate conversion and selectivity.

Figure 3:
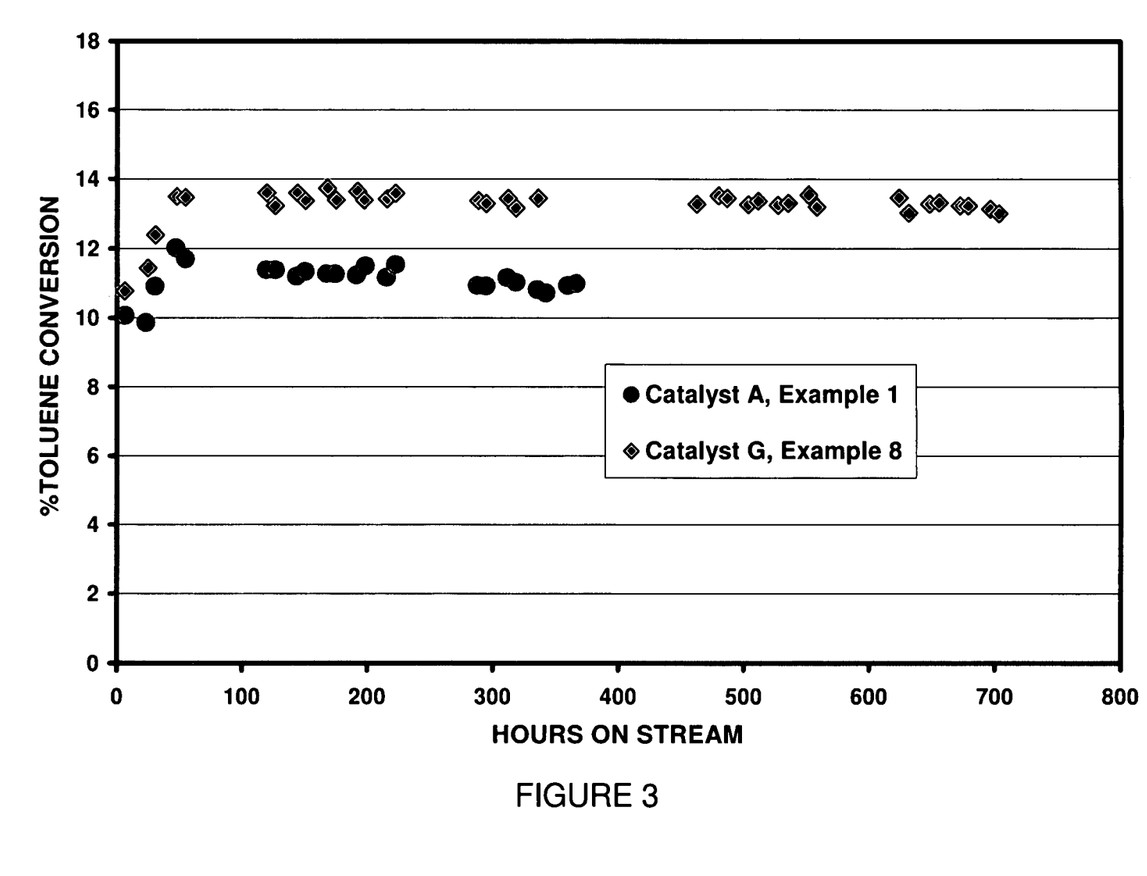
FIG. 3 shows a plot of toluene conversion over time for toluene methylation reactions using Catalyst A (without metal) from Example 1 and Catalyst G (containing nickel) from Example 8.

FIG. 3 shows catalyst activity as measured by toluene conversion at different time on stream over Catalyst G. For comparison toluene conversions obtained on Catalyst A are shown in FIG. 3. Also Table 2 shows toluene conversion, methanol conversion, toluene selectivity for mixed xylenes, para-xylene selectivity and methanol selectivity to mixed-xylenes for Catalyst G. Catalyst G showed higher activity than Catalyst A (without metal) but showed lower activity than Catalyst E (Example 5) which had roughly the same nickel content, but the procedure for Ni loading used non-evaporative separation of liquids and solids.

Example 9-11

Comparative Catalysts H-J

A "self-bound" P/ZSM-5 extruded catalyst was made by treating a $NH_4$-ZSM-5 zeolite powder having a $SiO_2/Al_2O_3$ mole ratio of between 250 and 300 with $H_3PO_4$ and made into an extrudable mixture, which was then extruded into 1/16-inch diameter cylindrical shaped extrudates. The extruded catalyst was then calcined or heated to a maximum temperature of 530° C. This formed Catalyst H. XRF analysis showed Catalyst H had the following composition: $SiO_2$ 77.65 wt %, $Al_2O_3$ 0.53 wt %, $P_2O_5$ 19.53 wt %, $Na_2O$<0.04 wt %. BET ($N_2$ adsorption) surface area and total pore volume of Catalyst H were 168 $m^2/g$ and 0.12 cc/g, respectively.

Several nickel loaded catalysts (I and J) were made using Catalyst H by treating it with different amounts of nickel using the same procedure as used for Catalysts B-F (see Table 4). The nickel contents of the Catalysts I and J were 0.08 wt % and 0.25 wt %, respectively, by total weight of catalyst.

TABLE 4

| Catalyst | (Extruded) Base Catalyst, g | Ni Salt, g | Water, ml | Aging Temp | Liquid Removal, Calcination | Wt % Ni by XRF |
|---|---|---|---|---|---|---|
| Catalyst H | Base Catalyst | N/A | N/A | N/A | N/A | N/A |
| Catalyst I | 32.093 | 0.323 | 100 | 60° C. | Decanted & Calcined at 530° C. | 0.08 |

TABLE 4-continued

| Catalyst | (Extruded) Base Catalyst, g | Ni Salt, g | Water, ml | Aging Temp | Liquid Removal, Calcination | Wt % Ni by XRF |
|---|---|---|---|---|---|---|
| Catalyst J | 32 | 0.739 | 100 | 60° C. | Decanted & Calcined at 530° C. | 0.25 |

Base Catalyst = Self Bound P/ZSM-5 Extruded Catalyst

Catalysts H, I and J were tested for toluene methylation reaction. Catalyst loading, predrying under $H_2$ flow and steaming conditions were the same as described for Example 3. After the catalyst drying at 480° C. and steaming at 200° C. overnight, a premixed toluene and methanol feed (molar ratio 3.0) was added to the reactor at 200° C. The liquid hourly space velocity (LHSV) [based on methylation feed (toluene+methanol)] was maintained at about 2 $hr^{-1}$ and a cofeed of $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig and the catalyst bed inlet temperature was increased to 450° C. and then adjusted to about 485° C. Reactor streams were analyzed to calculate conversion and selectivity.

Figure 4:
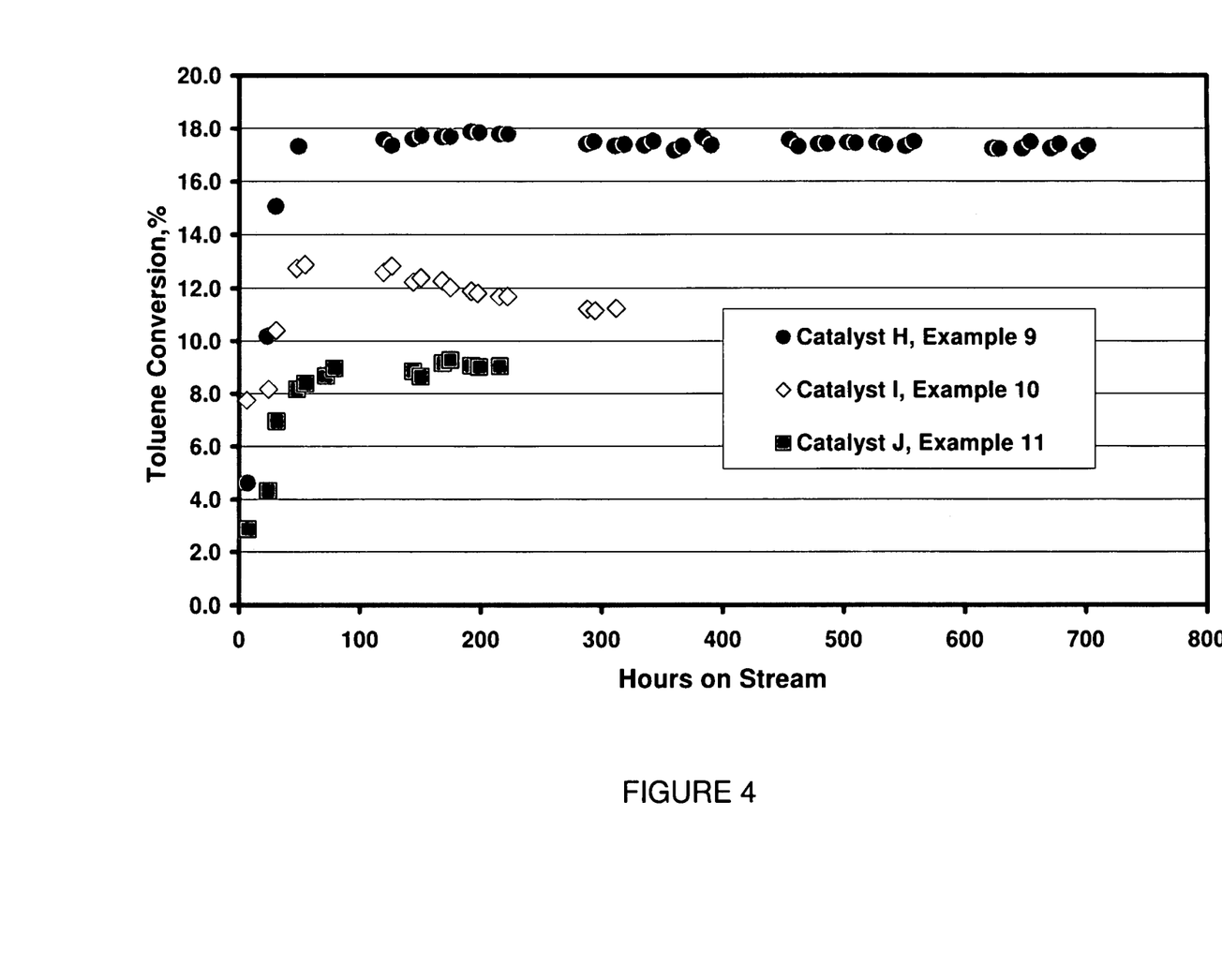
FIG. 4 shows a plot of toluene conversion over time for toluene methylation reactions using Catalyst H (self-bound P/ZSM-5 without metal) and Catalysts I and J (containing nickel) from Examples 9-11.

FIG. 4 shows toluene conversions at different time on stream for Catalysts H, I and J. Table 2 shows toluene conversion, methanol conversion, toluene selectivity for mixed xylenes, para-xylene selectivity and methanol selectivity to mixed xylenes for Catalysts H, I and J. Catalyst H, which was a self-bound P/ZSM-5 catalyst, showed toluene conversion of nearly 18 mole %, and toluene conversion declined slowly with time at a rate of −0.014% per 24 hours. Catalyst I, which contained about 0.08 wt % Ni, showed about 12.7% toluene conversion, which declined at a rate of about −0.170% per 24 hour. Catalyst J, which contained about 0.25 wt % Ni, showed significantly lower toluene conversion initially and reached about 9% toluene conversion. The run was discontinued because of the low activity, and the deactivation rate was not estimated.

In summary, the addition of Ni on self-bound P/ZSM-5 did not show increased catalyst activity or improved catalyst stability. This is in contrast to those with the addition of Ni on alumina bound P/ZSM-5 catalysts.

Example 12-14

Catalysts K-M

Pt-loaded P/ZSM-5 catalysts were made by adding various amounts of Pt on alumina bound P/ZSM-5 catalyst (Catalyst A) using the same procedure as used for Catalysts C, D, E and F. Catalyst A, described previously, was loaded with different loadings of platinum at 0.05, 0.11 and 0.18 wt % to form Catalysts K, L and M, respectively (see Table 5). The platinum was incorporated with the alumina bound P/ZSM-5 zeolite catalyst (Catalyst A) by dissolving different amounts of tetraamineplatinum (II) nitrate in about 100 ml of deionized water. Catalyst A (extrudates) was immersed in the platinum salt solution in a flask which was then shaken for 5 minutes and was aged at 60° C. overnight. Catalyst extrudate was separated from the aqueous liquid by decanting the liquid. The platinum-treated zeolites were then calcined at a maximum temperature of about 530° C. for 10 hours.

TABLE 5

| Catalyst | (Extruded) Base Catalyst, g | Metal Salt, g | Water, ml | Aging Temp | Liquid Removal, Calcination | Wt % Metal by XRF |
|---|---|---|---|---|---|---|
| Catalyst A | Base Catalyst | N/A | N/A | N/A | N/A | N/A |
| Catalyst K | 30.582 | 0.095 | 100 | 60° C. | Decanted & Calcined at 530° C. | 0.05% Pt |
| Catalyst L | 30.403 | 0.155 | 100 | 60° C. | Decanted & Calcined at 530° C. | 0.11% Pt |
| Catalyst M | 30.088 | 0.305 | 100 | 60° C. | Decanted & Calcined at 530° C. | 0.18% Pt |
| Catalyst N | 30.407 | 1.622 | 100 | 60° C. | Decanted & Calcined at 530° C. | 0.05% Pd |
| Catalyst O | 30.105 | 3.245 | 100 | 60° C. | Decanted & Calcined at 530° C. | 0.09% Pd |

Base Catalyst = Alumina Bound P/ZSM-5 Extruded Catalyst

Each of Catalysts K, L and M were tested in toluene methylation reactions. Catalyst loading, heating under $H_2$ flow and steaming conditions were the same as described for Catalyst B in Example 3. After the catalyst drying at 480° C. and steaming at 200° C. overnight, a premixed toluene and methanol feed (molar ratio 4.5) was added to the reactor at 200° C. The liquid hourly space velocity (LHSV) [based on methylation feed (toluene+methanol)] was maintained at about 2 $hr^{-1}$ and a cofeed $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig and the catalyst bed inlet temperature was increased to 450° C. and then adjusted to about 485° C. Reactor streams were analyzed to calculate conversion and selectivity.

Figure 5:
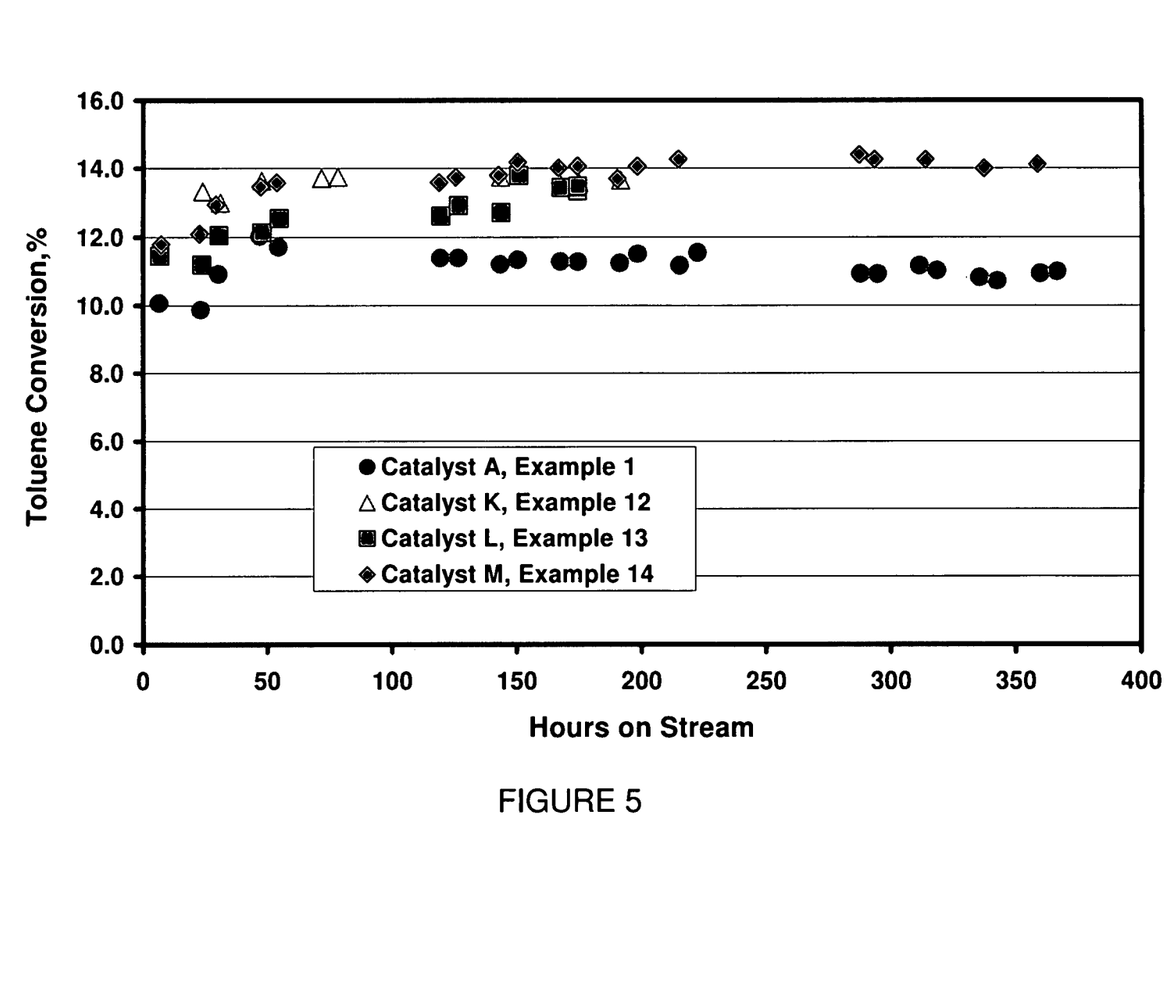
FIG. 5 shows a plot of toluene conversion over time for toluene methylation reactions using Catalyst A (without metal) from Example 1 and Catalysts K-M (containing platinum) from Examples 12-14.

FIG. 5 shows the comparison of toluene conversion using Catalysts K-M containing different amounts of platinum and Catalyst A containing no metal. Table 6 shows toluene conversion, methanol conversion, toluene selectivity for mixed xylenes, para-xylene selectivity and methanol selectivity to mixed xylenes for Catalysts A and K-M. Compared to Catalyst A, all three platinum-containing Catalysts K, L and M showed increased catalyst activity showing higher toluene conversions and showed no apparent decline in toluene conversion during the test period.

Example 15-16

Catalysts N-O

Pd-loaded P/ZSM-5 catalysts were made by adding various amounts of Pd on alumina bound P/ZSM-5 catalyst (Catalyst A) using the same procedure as used for Catalysts C, D, E and F. Catalyst A, described previously, was loaded with different loadings of palladium at 0.05 and 0.09 wt % to form Catalysts N and O, respectively (see Table 5). The palladium was incorporated with the alumina bound P/ZSM-5 zeolite catalyst (Catalyst A) by dissolving different amounts of palladium nitrate in about 100 ml of deionized water. Catalyst A (extrudates) was immersed in the palladium salt solution in a flask, which was then shaken for 5 minutes and was aged at 60° C. overnight. Catalyst extrudate was separated from the aqueous liquid by decanting the liquid. The palladium loaded catalysts were then calcined at a maximum temperature of about 530° C. for 10 hours.

Each of Catalysts N and O were tested in toluene methylation reactions. Catalyst loading, heating under $H_2$ flow and steaming conditions were the same as described for Catalyst B in Example 3. After treating the catalyst under $H_2$ flow at 480° C. for 3 hours and steaming at 200° C. overnight, a premixed toluene and methanol feed (molar ratio 4.5) was added to the reactor at 200° C. The liquid hourly space velocity (LHSV) [based on methylation feed (toluene+methanol)] was maintained at about 2 $hr^{-1}$ and a cofeed $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig and the catalyst bed inlet temperature was increased to 450° C. and then adjusted to about 485° C. Reactor streams were analyzed to calculate conversion and selectivity.

Figure 6:
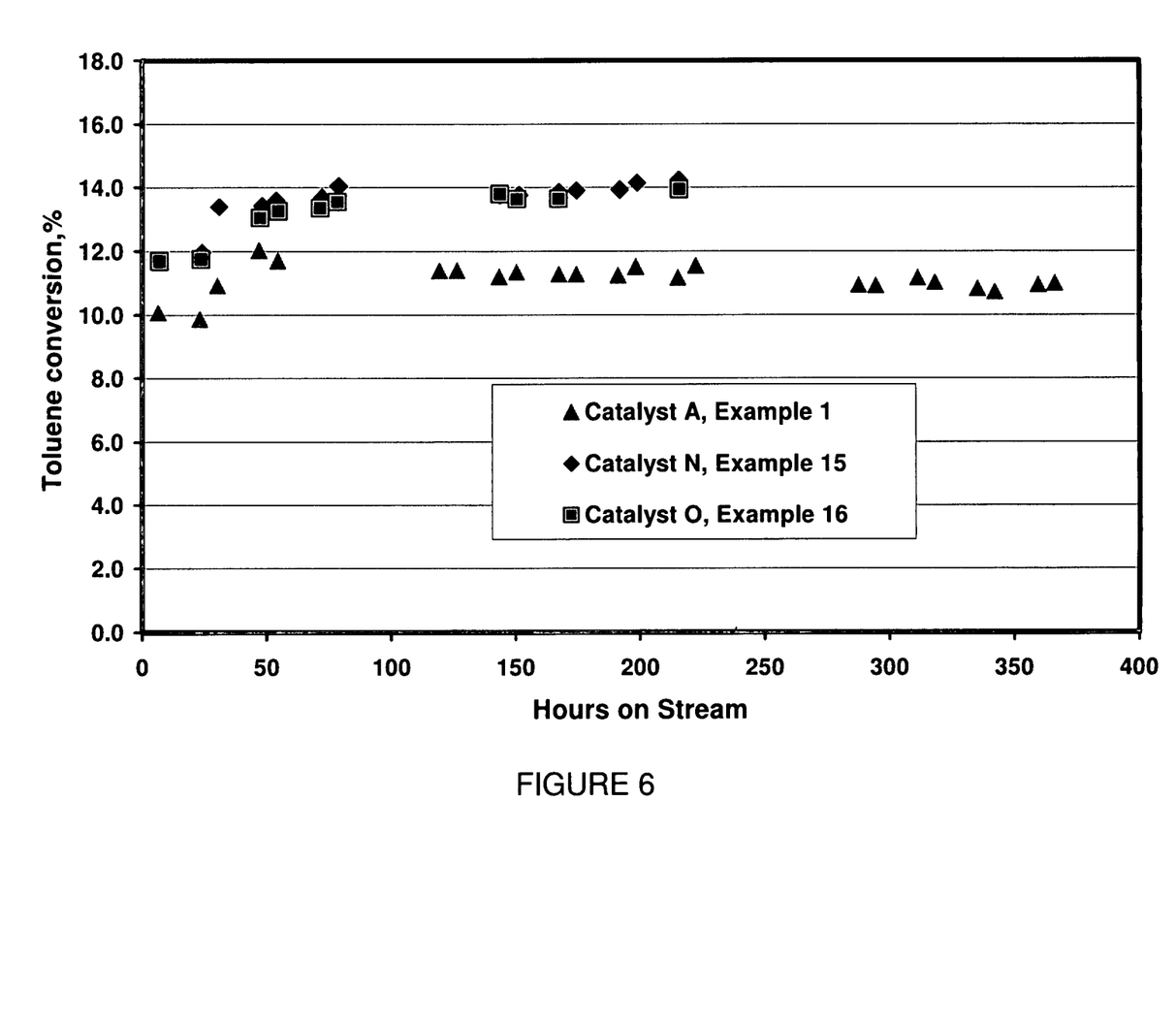
FIG. 6 shows a plot of toluene conversion over time for the toluene methylation reactions using Catalysts A (without metal) from Example 1 and Catalysts N-O (containing palladium) from Examples 15-16.

Table 6 shows toluene conversion, methanol conversion, toluene selectivity for mixed xylenes, para-xylene selectivity and methanol selectivity to mixed xylenes for Catalysts A and N-O. FIG. 6 shows the comparison of toluene conversion using Catalysts N and O containing palladium and Catalyst A containing no metal. Compared to Catalyst A, both the palladium-containing Catalysts N and O showed increased catalyst activity with higher toluene conversions and showed no apparent decline in toluene conversion during the test period.

Table 7 shows the comparison of toluene conversion and catalyst deactivation rate (toluene conversion decline rate per 24 hours at constant catalyst bed inlet temperature) between Catalyst A (no metal), Catalyst G (0.10 wt % Ni), Catalyst E (0.09 wt % Ni), Catalyst L (0.11 wt % Pt), Catalyst 0 (0.09 wt % Pd) having almost the same amount of metal on base Catalyst A. Catalyst G was made using the commonly used impregnation technique (evaporated the solution) and showed an increased toluene conversion compared to base Catalyst A (13.5% for Catalyst G versus 11.5% for Catalyst A, which is about a 17% relative increase in activity). Catalyst G also showed improved deactivation rate (−0.012% for Catalyst G versus −0.065% for Catalyst A). Whereas Catalyst E, which was made by decanting Ni salt solution, showed a further increased toluene conversion (14.9% for Catalyst E versus 11.5% for Catalyst A and 13.5% for Catalyst G) and toluene conversion did not decline during the testing period. Catalyst L (0.11 wt % Pt) and Catalyst O (0.09 wt % Pd) made by using the same method as used for Catalyst E (0.09% Ni) showed increased activity compared to base Catalyst A but not as much as for Catalyst E. Like Catalyst E, Catalysts L and O showed no decline in toluene conversion during the testing period.

TABLE 7

| | Catalyst Description | | | | Performance Test | |
| --- | --- | --- | --- | --- | --- | --- |
| Catalyst | Base | Metal | Method | $X_{Tol}$ | Relative Activity Increase[1] | Deactivation Rate[2] |
| Catalyst A | $Al_2O_3$-P/ZSM-5 (Catalyst A) | 0 | "As-is" | 11.5 | Base Case | −0.065 |
| Catalyst G | $Al_2O_3$-P/ZSM-5 (Catalyst A) | 0.10% Ni | Impregnated | 13.5 | 17% | −0.012 |
| Catalyst E | $Al_2O_3$-P/ZSM-5 (Catalyst A) | 0.09% Ni | Aged & Decanted | 14.9 | 34% | Not observed |
| Catalyst L | $Al_2O_3$-P/ZSM-5 (Catalyst A) | 0.11% Pt | Aged & Decanted | 13.5 | 17% | Not observed |
| Catalyst O | $Al_2O_3$-P/ZSM-5 (Catalyst A) | 0.09% Pd | Aged & Decanted | 13.6 | 18% | Not observed |
| Catalyst H | P/ZSM-5 (Catalyst H) | 0 | "As-is" | 17.7 | Base Case | −0.014 |
| Catalyst I | P/ZSM-5 (Catalyst H) | 0.08% Ni | Aged & Decanted | 12.7 | −28% | −0.170 |

$X_{Tol}$ = Toluene conversion, mole %.
[1]Relative activity increase of a catalyst is estimated by comparing toluene conversion obtained on the catalyst compared to that on base catalyst.
[2]Deactivation rate: Toluene conversion decline, mole % per 24 hour.

Table 7 also shows the comparison of toluene conversion and catalyst deactivation rate between Catalyst H (no metal) and Catalyst I (0.08 wt % Ni). Catalyst H is a self-bound P/ZSM-5 catalyst. Catalyst I was made by using Catalyst H and by using the same method as used for Catalyst E. Unexpectedly, Catalyst I did not show any increase in activity, but rather it showed a dramatic decrease in activity, and toluene conversion declined faster than for the base Catalyst H.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

TABLE 2

| Example# | Catalyst | Base Catalyst | Metal | Method | Drying Temp/°C. | T/°C. | $X_{Tol}$ | $X_{MeOH}$ | $S_{MX}$ | $S_{PX}$ | $S_{MeOH}$ |
|---|---|---|---|---|---|---|---|---|---|---|---|
| 1 | Catalyst A | Al$_2$O$_3$-P/ZSM-5 | 0 | "As-is" | 480 | 485 | 11.4 | 96 | 97.8 | 96.6 | 53.8 |
| 2-3 | Catalyst B | Al$_2$O$_3$-P/ZSM-5 (Catalyst A) | 0.07% Ni | Aged & Decanted | 430 | 488 | 15.4 | 100 | 96.5 | 90.3 | 70 |
|  |  |  |  |  | 480 | 485 | 15.4 | 100 | 97.0 | 91.6 | 73 |
| 4 | Catalyst C | Al$_2$O$_3$-P/ZSM-5 (Catalyst A) | 0.03% Ni | Aged & Decanted | 480 | 486 | 14.9 | 100 | 96.7 | 87.2 | 65.8 |
| 5 | Catalyst D | Al$_2$O$_3$-P/ZSM-5 (Catalyst A) | 0.04% Ni | Aged & Decanted | 480 | 486 | 14.4 | 100 | 95.4 | 87.5 | 62.6 |
| 6 | Catalyst E | Al$_2$O$_3$-P/ZSM-5 (Catalyst A) | 0.09% Ni | Aged & Decanted | 480 | 486 | 14.9 | 100 | 96.1 | 85.5 | 65.6 |
| 7 | Catalyst F | Al$_2$O$_3$-P/ZSM-5 (Catalyst A) | 0.15% Ni | Aged & Decanted | 480 | 485 | 14.7 | 100 | 96.9 | 90.8 | 65 |
| 8 | Catalyst G | Al$_2$O$_3$-P/ZSM-5 (Catalyst A) | 0.10% Ni | Impregnated | 480 | 485 | 13.5 | 100 | 97.9 | 95.1 | 60 |
| 9 | Catalyst H | P/ZSM-5 | 0 | "As-is" | 480 | 496 | 17.7 | 91 | 95.3 | 86.4 | 57 |
| 10 | Catalyst I | P/ZSM-5 (Catalyst H) | 0.08% Ni | Aged & Decanted | 480 | 498 | 12.7 | 86 | 97.3 | 96.1 | 45 |
| 11 | Catalyst J | P/ZSM-5 (Catalyst H) | 0.25% Ni | Aged & Decanted | 480 | 497 | 8.4 | 79 | 96.2 | 91.9 | 34 |

$X_{Tol}$ = Toluene conversion, mole %;
$X_{MeOH}$ = Methanol conversion, mole %;
$S_{MX}$ = Toluene selectivity to mixed-Xylene;
$S_{PX}$ = p-xylene selectivity;
$S_{MeOH}$ = Methanol selectivity to mixed-xylenes

TABLE 6

| Example# | Catalyst | Base Catalyst | Metal | Method | Drying Temp/°C. | T/°C. | $X_{Tol}$ | $X_{MeOH}$ | $S_{MX}$ | $S_{PX}$ | $S_{MeOH}$ |
|---|---|---|---|---|---|---|---|---|---|---|---|
| 1 | Catalyst A | Al$_2$O$_3$-P/ZSM-5 | 0 | "As-is" | 480 | 485 | 11.5 | 96 | 97.8 | 96.6 | 53.8 |
| 12 | Catalyst K | Al$_2$O$_3$-P/ZSM-5 (Catalyst A) | 0.05% Pt | Aged & Decanted | 480 | 486 | 13.9 | 96.6 | 96.2 | 90.7 | 62.7 |
| 13 | Catalyst L | Al$_2$O$_3$-P/ZSM-5 (Catalyst A) | 0.11% Pt | Aged & Decanted | 480 | 486 | 13.5 | 97.3 | 98.3 | 91.2 | 62.3 |
| 14 | Catalyst M | Al$_2$O$_3$-P/ZSM-5 (Catalyst A) | 0.18% Pt | Aged & Decanted | 480 | 486 | 14.5 | 97.3 | 98.3 | 90.4 | 63.0 |
| 15 | Catalyst N | Al$_2$O$_3$-P/ZSM-5 (Catalyst A) | 0.05% Pd | Aged & Decanted | 480 | 485 | 14.0 | 100 | 97.2 | 90.2 | 61.9 |
| 16 | Catalyst O | Al$_2$O$_3$-P/ZSM-5 (Catalyst A) | 0.09% Pd | Aged & Decanted | 480 | 486 | 13.6 | 100 | 97.7 | 91.5 | 60.7 |

$X_{Tol}$ = Toluene conversion, mole %;
$X_{MeOH}$ = Methanol conversion, mole %;
$S_{MX}$ = Toluene selectivity to mixed-Xylene;
$S_{PX}$ = p-xylene selectivity;
$S_{MeOH}$ = Methanol selectivity to mixed-xylenes

We claim:

1. A hydrogenating-metal-containing zeolite catalyst for use in aromatic alkylation, the catalyst formed by
    treating a ZSM-5 zeolite with a phosphorus-containing compound to form a phosphorus-treated zeolite;
    combining the phosphorus-treated zeolite with a binder material to form a bound phosphorus-treated zeolite;
    treating the bound phosphorus-treated zeolite with an aqueous solution of a hydrogenating metal compound by contacting the bound phosphorus-treated zeolite with the aqueous solution to form a hydrogenating-metal-containing zeolite in an aqueous medium, wherein the hydrogenating metal is Group VIII transition metal;
    separating the aqueous medium from the bound phosphorus-treated zeolite using a non-evaporative separation technique; and
    calcining to form a hydrogenating-metal-containing zeolite catalyst.

2. The catalyst of claim 1, wherein:
    the hydrogenating metal is selected from at least one of nickel, palladium and platinum.

3. The catalyst of claim 1, wherein:
    the calcining is at a temperature of about 400° C. or higher.

4. The catalyst of claim 1, wherein:
    the hydrogenating metal is present in the catalyst in an amount of about 0.03% to about 5% by total weight of catalyst.

5. The catalyst of claim 1, wherein:
    the catalyst contains about 0.01% to about 15% phosphorus by total weight of catalyst.

6. The catalyst of claim 1, wherein:
    the binder comprises an alumina binder.

7. The catalyst of claim 1, wherein:
    the binder is present in the catalyst in an amount of about 1% to about 99% by total weight of the catalyst.

8. The catalyst of claim 2, wherein the hydrogenating metal comprises nickel.

9. The catalyst of claim 8, wherein the nickel is present in the catalyst in an amount of about 0.01% to about 5% by total weight of the catalyst.

10. The catalyst of claim 9, wherein the nickel is present in the catalyst in an amount of about 0.03% to about 2.0% by total weight of the catalyst.

11. The catalyst of claim 8, wherein:
the catalyst contains about 0.01% to about 15% phosphorus by total weight of catalyst; and
the binder comprises an alumina binder.

12. The catalyst of claim 1, wherein the temperature of the aqueous solution is maintained at a temperature below the boiling point of the aqueous solution.

13. The catalyst of claim 12, wherein the temperature of the aqueous solution is maintained at room temperature.

14. The catalyst of claim 1, wherein the non-evaporative separation technique comprises decanting.

15. A method of forming a hydrogenating-metal-containing zeolite catalyst for use in aromatic alkylation, the method comprising:
treating a ZSM-5 zeolite with a phosphorus-containing compound to form a phosphorus-treated zeolite;
combining the phosphorus-treated zeolite with a binder material to form a bound phosphorus-treated zeolite;
treating the bound phosphorus-treated zeolite with an aqueous solution of a hydrogenating metal compound by contacting the bound phosphorus-treated zeolite with the aqueous solution to form a hydrogenating-metal-containing zeolite in an aqueous medium, wherein the hydrogenating metal is Group VIII transition metal;
separating the aqueous medium from the bound phosphorus-treated zeolite using a non-evaporative separation technique; and
calcining to form the hydrogenating-metal-containing zeolite catalyst.

16. The method of claim 15, wherein the temperature of the aqueous solution is maintained at a temperature below the boiling point of the aqueous solution.

17. The method of claim 16, wherein the temperature of the aqueous solution is maintained at room temperature.

18. The method of claim 15, wherein the non-evaporative separation technique comprises decanting.

19. The method of claim 15, wherein the hydrogenating metal is selected from at least one of nickel, palladium, and platinum.

20. The method of claim 19, wherein the hydrogenating metal comprises nickel.

21. The method of claim 20, wherein the nickel is present in the catalyst in an amount of about 0.03% to about 2% by total weight of catalyst.

22. The method of claim 15, wherein the catalyst contains about 0.01% to about 15% phosphorus by total weight of catalyst.

* * * * *